United States Patent

Katner

[11] 4,200,745
[45] Apr. 29, 1980

[54] 7[2-(2-AMINOTHIAZOL-4-YL)-2-ALKOXYIMINO]ACETAMIDO 3[4-ALKYL-5-OXO-6-HYDROXY-3,4 DIHYDRO 1,2,4-TRIAZIN 3-YL]THIO METHYL CEPHALOSPORINS

[75] Inventor: Allen S. Katner, Indianapolis, Ind.

[73] Assignee: Eli Lilly and Company, Indianapolis, Ind.

[21] Appl. No.: 862,318

[22] Filed: Dec. 20, 1977

[51] Int. Cl.$^2$ ............................................. C07D 501/36
[52] U.S. Cl. ........................................ 544/21; 544/27
[58] Field of Search ................................. 544/21, 27

[56]     References Cited
    FOREIGN PATENT DOCUMENTS 831787  1/1976  Belgium .
852860  9/1977  Belgium .

Primary Examiner—Donald G. Daus
Assistant Examiner—David E. Wheeler
Attorney, Agent, or Firm—Steven R. Lammert; Arthur R. Whale

[57]                ABSTRACT

Cephalosporin compounds of the formula

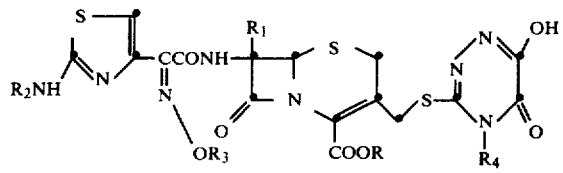

wherein R and $R_2$ are hydrogen or protecting groups, $R_1$ is hydrogen or methoxy, $R_3$ is hydrogen or $C_1$-$C_4$ alkyl and $R_4$ is $C_1$-$C_4$ alkyl, are broad spectrum antibiotics or intermediates thereto.

12 Claims, No Drawings

7[2-(2-AMINOTHIAZOL-4-YL)-2-ALKOX-YIMINO]ACETAMIDO 3[4-ALKYL-5-OXO-6-HYDROXY-3,4 DIHYDRO 1,2,4-TRIAZIN 3-YL]THIO METHYL CEPHALOSPORINS

BACKGROUND AND SUMMARY OF THE INVENTION

A considerable research effort has been directed to the development of new cephalosporin compounds for the treatment of infectious diseases in man. Most recently it has been disclosed that certain cephalosporins bearing a 2-(2-aminothiazol-4-yl)-2-methoxyiminoacetamido substituent at C-7 and substituents including acetoxymethyl, carbamoyloxymethyl, (1-methyl-tetrazol-5-ylthio)methyl and (1,3,4-thiadiazol-2-ylthio)methyl at C-3, exhibit activity against both Gram positive and Gram negative microorganisms (Belgian Patent Nos. 852,860, 852,971, 850,662 and 853,545, West German Offen. No. 2,704,712, and Japanese Application No. 125,826/1976).

This invention relates to a new class of cephalosporin compounds. More particularly this invention relates to cephalosporins having a 2-(2-aminothiazol-4-yl)-2-(hydroxy or $C_1$–$C_4$ alkoxy)iminoacetamido group at C-7 and a 4-($C_1$–$C_4$ alkyl)-5-oxo-6-hydroxy-4,5-dihydro-1,2,4-triazin-3-ylthio)-methyl group at C-3. The compounds of this invention exhibit excellent broad spectrum Gram positive and Gram negative antibiotic activity. The present compounds exhibit superior antibiotic activity, especially against Gram positive microorganisms, when compared with other cephalosporin compounds, including the recently disclosed cephalosporins having a C-7 2-(2-aminothiazol-4-yl)-2-alkoxyiminoacetamido substituent.

Broadly the compounds of this invention have the formula

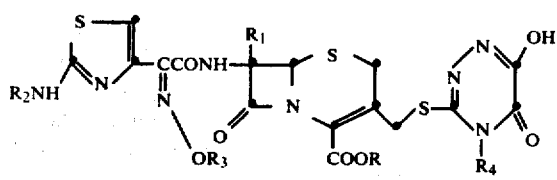

wherein R is hydrogen, an alkali metal cation, or a carboxylic acid protecting group; $R_1$ is hydrogen or methoxy; $R_2$ is hydrogen or an amino protecting group; $R_3$ is hydrogen or $C_1$–$C_4$ alkyl; and $R_4$ is $C_1$–$C_4$ alkyl.

DETAILED DESCRIPTION OF THE INVENTION

In the above formula representing the compounds of the present invention $R_3$ is hydrogen or $C_1$–$C_4$ alkyl and $R_4$ is $C_1$–$C_4$ alkyl. By "$C_1$–$C_4$ alkyl" is meant methyl, ethyl, n-propyl, isopropyl, n-butyl, sec-butyl, isobutyl or tert-butyl. Preferably $R_3$ is methyl. Preferred groups represented by $R_4$ are methyl and ethyl. Most preferably $R_4$ is methyl.

Examples of the resulting C-3 substituent of the cephalosporin compounds of the present invention in which $R_4$ is as defined above include 4-methyl-5-oxo-6-hydroxy-4,5-dihydro-1,2,4-triazin-3-ylthiomethyl; 4-ethyl-5-oxo-6-hydroxy-4,5-dihydro-1,2,4-triazin-3-ylthiomethyl; 4-n-propyl-5-oxo-6-hydroxy-4,5-dihydro-1,2,4-triazin-3-ylthiomethyl; 4-isopropyl-5-oxo-6-hydroxy-4,5-dihydro-1,2,4-triazin-3-ylthiomethyl; 4-n-butyl-5-oxo-6-hydroxy-4,5-dihydro-1,2,4-triazin-3-ylthiomethyl; 4-sec-butyl-5-oxo-6-hydroxy-4,5-dihydro-1,2,4-triazin-3-ylthiomethyl; 4-isobutyl-5-oxo-6-hydroxy-4,5-dihydro-1,2,4-triazin-3-ylthiomethyl; and the like.

In the above formula R is hydrogen, an alkali metal cation, or a carboxylic acid protecting group. The term "a carboxylic acid protecting group" refers to any group used to block or protect the cephalosporin C-4 carboxylic acid functionality while reactions involving other functional sites are carried out. Such carboxylic acid protecting groups are noted for their ease of cleavage, as for example by hydrolytic or hydrogenolytic methods to the corresponding carboxylic acid. Examples of suitable carboxylic acid protecting groups are tert-butyl, 1-methylcyclohexyl, benzyl, 4-methoxybenzyl, 4-nitrobenzyl, acetoxymethyl, 1-acetoxyethyl, pivaloyloxymethyl, 1-pivaloyloxyethyl, carboethoxyoxymethyl, 1-carboethoxyoxyethyl, phthalidyl, 2-iodoethyl, 2-bromoethyl, benzhydryl, phenacyl, 4-halophenacyl, dimethylallyl, 2,2-trichloroethyl, methoxymethyl, tri($C_1$–$C_3$ alkyl)silyl and succinimidomethyl. Other known carboxylic acid protecting groups are described by E. Haslam in "Protective Groups in Organic Chemistry," J. F. W. McOmie, Ed., Plenum Press, New York, 1973, Chapter 5. The nature of such groups is not critical; however, because of availability, ease of handling and other desirable properties, certain carboxylic acid protecting groups are preferred. A preferred selection of carboxylic acid protecting groups includes acetoxymethyl, 1-acetoxyethyl, pivaloyloxymethyl, 1-pivaloyloxyethyl, carboethoxyoxymethyl, 1-carboxyethoxyoxyethyl and phthalidyl. Another preferred group of carboxy protecting entities comprises benzhydryl and tert-butyl. Most preferred is benzhydryl.

Most preferred of the groups represented by R is hydrogen; the free acids represented by the compounds in which R is hydrogen and the corresponding alkali metal salts, such as the sodium, potassium and lithium salts, are the most active of the compounds of the present invention. Compounds of the present invention where R is a carboxylic acid protecting group are useful primarily as intermediates to the free acids and their alkali metal salts. In addition to serving as intermediates to the free acids, however, the present compounds wherein R is acetoxymethyl, 1-acetoxyethyl, pivaloyloxymethyl, 1-pivaloyloxyethyl, carboethoxyoxymethyl, 1-carboethoxyoxyethyl and phthalidyl show enhanced absorbability, resulting in higher blood levels, over the free acids of the present invention when employed in nonparenteral antibiotic administrations.

$R_2$ in the above formula representing the compounds of the present invention is hydrogen or an amino protecting group; hydrogen is preferred. The term "an amino protecting group" refers to those groups which can be employed to block or protect the amino group while reactions involving other functional sites are carried out. Many amino protecting groups and their preparation and properties are known to those skilled in the art. Examples of suitable amino protecting groups are chloroacetyl, 4-nitrobenzyloxycarbonyl, 2,2,2-trichloroethoxycarbonyl, tert-butyloxycarbonyl, benzyloxycarbonyl, and trityl. Like conventional amino protecting groups such as those described by J. W. Barton in "Protective Groups in Organic Chemistry,"

J. F. W. McOmie, Ed., Plenum Press, New York, 1973, Chapter 2, are suitable. Preferred amino protecting groups are tert-butyloxycarbonyl, benzyloxycarbonyl and trityl. Trityl is most preferred.

The C-7 side chain substituent on the present cephalosporin compounds is a 2-[2-(protected)aminothiazol-4-yl]-2-(hydroxy or $C_1$-$C_4$ alkoxy)iminoacetamido group. In regard to the configuration of the hydroxyimino group or the alkoxyimino group, in relation to the adjacent carboxamido functionality, the compounds can exist as the syn (cis) isomer or anti isomer. The syn isomers are preferred in the present invention. The syn configuration is structurally denoted in the present specification as indicated in the following partial structure:

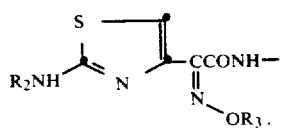

The following are exemplary of the C-7 side chain substituent of the present cephalosporin compounds wherein $R_2$ and $R_3$ are as defined above:

2-(2-aminothiazol-4-yl)-2-methoxyiminoacetamido, 2-(2-aminothiazol-4-yl)-2-ethoxyiminoacetamido, 2-(2-tritylaminothiazol-4-yl)-2-isopropoxyiminoacetamido, 2-(2-aminothiazol-4-yl)-2-n-propoxyiminoacetamido, 2-(2-tert-butyloxycarbonylaminothiazol-4-yl)-2-sec-butoxyiminoacetamido, 2-(2-benzyloxycarbonylaminothiazol-4-yl)-2-hydroxyiminoacetamido.

2-[2-(2-chloroacetamido)thiazol-4-yl]-2-methoxyiminoacetamido, 2-(2-aminothiazol-4-yl)-2-hydroxyiminoacetamido, 2-(2-tritylaminothiazol-4-yl)-2-ethoxyiminoacetamido, 2-[2-(2,2,2-trichloroethoxycarbonylamino)thiazol-4-yl]-2-isopropoxyiminoacetamido, 2-(2-aminothiazol-4-yl)-2-n-butoxyiminoacetamido, 2-(2-aminothiazol-4-yl)-2-isopropoxyiminoacetamido, and 2-(2-benzyloxycarbonylaminothiazol-4-yl)-2-methoxyiminoacetamido.

It should be noted that the compounds of the present invention can tautomerize both at the 2-aminothiazol-4-yl group on the C-7 side chain and at the 1,2,4-triazin-3-yl moiety at C-3. The possible tautomerization of each of these entities is illustrated by the partial structures hereinbelow.

At C-7:

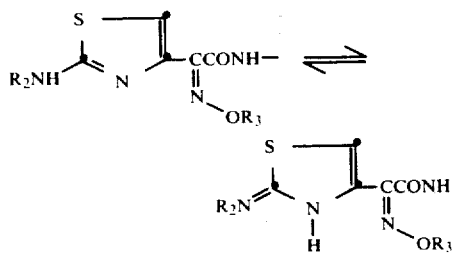

At C-3:

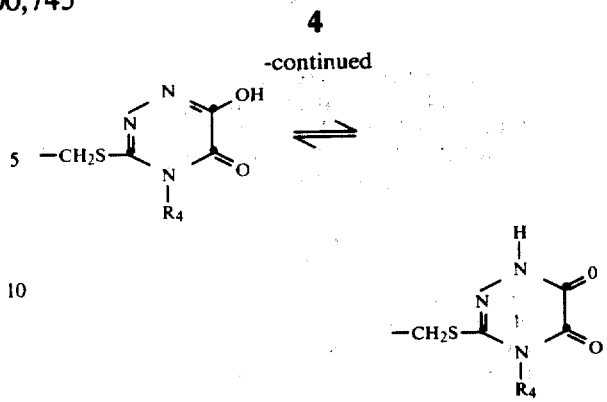

For the purpose of the present invention molecular structures, when drawn to one structure, shall be construed to represent also its tautomeric forms.

The compounds of the present invention are prepared by acylating cephalosporin nucleus and nucleus ester compounds of the formula

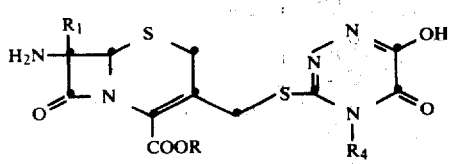

wherein R, $R_1$ and $R_4$ are as defined hereinabove with acylating agents derived from substituted acetic acids of the formula

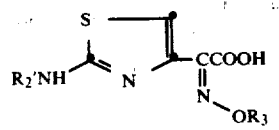

wherein $R_2'$ is an amino protecting group and $R_3$ is as defined above. The acylation can be accomplished using any one of a number of conventional acylating techniques recognized in the cephalosporin art. Acylation of the nucleus esters and especially the benzhydryl ester has yielded good results.

The above depicted 3-[4-($C_1$-$C_4$ alkyl)-5-oxo-6-hydroxy-4,5-dihydro-1,2,4-triazin-3-ylthio]methyl cephalosporin nucleus and nucleus esters are prepared in accordance with the procedures described in Belgian Pat. No. 831,786, issued Jan. 28, 1976. In general the required cephalosporin nucleus and nucleus esters are prepared by (1) the well-known aqueous nucleophilic displacement of the C-3' acetoxy group from known acetoxymethyl cephalosporin acids; (2) cleavage of the existing C-7 acylamino group using the particular conventional method ($PCl_5$ cleavage, hydrogenation, acid hydrolysis, etc.) known by those skilled in the art to be best suited for removal of that particular group; and if the nucleus ester is desired (3) esterifying the nucleus with the desired esterifying agent, such as a diazoalkane, alcohol, or arylalkyl halide.

The required 3-mercapto-4-($C_1$-$C_4$ alkyl)-5-oxo-6-hydroxy-4,5-dihydro-1,2,4-triazine used in the acetoxy displacement step is prepared from an appropriately substituted thiosemicarbazide and diethyl oxalate in the presence of sodium ethoxide in accordance with the procedure described by Pesson et al., *Bulletin de la Societe Chemique de France*, (1970) pages 1590–1599.

The 7-methoxy-3-[4-($C_1$-$C_4$ alkyl)-5-oxo-6-hydroxy-4,5-dihydro-1,2,4-triazin-3-ylthio]methyl cephalosporin nucleus and nucleus ester precursors for the preparation of the present 7-methoxy cephalosporin compounds can be prepared from 7-methoxy-3-acetoxymethylcephalosporin compounds by a route similar to that described in the foregoing paragraph for the non-methoxylated starting materials. The 7-methoxy-3-acetoxymethyl cephalosporin starting materials can be prepared in accordance with the method described by G. A. Koppel and R. E. Koehler, *Journal of the American Chemical Society*, 95, 2403 (1973). After nucleophilic displacement of the C-3'-acetoxy group, the 7-acylamino group can be cleaved in accordance with the non-aqueous procedure of Lunn et al., *Tetrahedron Letters*, No. 14, pp. 1307–1310 (1974).

Preferably the 7-methoxy-3-[4-($C_1$-$C_4$ alkyl)-5-oxo-6-hydroxy-4,5-dihydro-1,2,4-triazin-3-ylthio]methyl cephalosporin nucleus precursor for the present 7-methoxy compounds can be prepared from the 7-methoxy-3-chloromethylcephalosporins described in U.S. Pat. No. 4,048,163, issued Sept. 13, 1977. Non-aqueous nucleophilic displacement of the C-3' chloro group in, for example, dimethylformamide by the aforedescribed 3-mercapto-1,2,4-triazine, followed by a non-aqueous $PCl_5$ cleavage of the 7-acylamino group provides the desired 7-methoxy cephalosporin nucleus, which upon reacylation, provides the present 7-methoxy cephalosporin compounds.

The 2-[2-(protected)aminothiazol-4-yl]-2-($C_1$-$C_4$ alkoxy or hydroxy)iminoacetic acids used to acylate the aforedescribed 3-triazinylthiomethyl cephalosporin nucleus substrates are prepared in accordance with the procedures described in Belgian Patent No. 850,662. Generally the iminoacetic acids are derived from ethyl 2-acetyl-2-hydroxyiminoacetate by (1) optional alkylation of the hydroxyimino functionality; (2) bromination with bromine in methylene chloride at room temperature to provide ethyl 2-(α-bromoacetyl)-2-hydroxyimino or $C_1$-$C_4$ alkoxyimino)-acetate; (3) reaction with thiourea in aqueous ethanol to provide ethyl 2-(2-aminothiazol-4-yl)-2-hydroxyimino or $C_1$-$C_4$ alkoxyimino)acetate; (4) blocking of the 2-amino group with an amino protecting group; and (5) base catalyzed deesterification. The 2-[2-(protected) aminothiazol-4-yl]-2-(hydroxy or $C_1$-$C_4$ alkoxy)iminoacetic acid, thus prepared, is then employed to acylate the aforedescribed cephalosporin nucleus or nucleus ester.

The acylation is typically accomplished using a coupling reagent such as dicyclohexylcarbodiimide in an inert organic solvent such as chloroform or methylene chloride. The product isolated from the acylation mixture can then be subjected to reaction conditions known by those skilled in the art to remove both the particular amino protecting group (on the 2-aminothiazol-4-yl group) and, either concomitantly or subsequently, the carboxylic acid protecting group (present if a nucleus ester was employed in the preparation). It is advantageous in the preparation of the present compounds that the particular amino and carboxylic acid protecting groups employed in the synthesis of any given compound of the present invention be chosen so that cleavage of both protecting groups can be achieved under one set of reaction conditions.

The resulting reaction product can be separated from the reaction mixture by a variety of conventional methods including crystallization, trituration, and chromatography, especially chromatography on ion-exchange resins.

Exemplary of the biologically active 7-methoxycephalosporin compounds of the present invention are 7-[2-(2-aminothiazol-4-yl)-2-methoxyiminoacetamido]-7-methoxy-3-(4-methyl-5-oxo-6-hydroxy-4,5-dihydro-1,2,4-triazin-3-ylthio)methyl-3-cephem-4-carboxylic acid, 7-[2-(2-aminothiazol-4-yl)-2-hydroxyiminoacetamido]-7-methoxy-3-(4-ethyl-5-oxo-6-hydroxy-4,5-dihydro-1,2,4-triazin-3-ylthio)methyl-3-cephem-4-carboxylic acid, 7-[2-(2-aminothiazol-4-yl)-2-ethoxyiminoacetamido]-7-methoxy-3-(4-isopropyl-5-oxo-6-hydroxy-4,5-dihydro-1,2,4-triazin-3-ylthio)methyl-3-cephem-4-carboxylic acid, 7-[2-(2-aminothiazol-4-yl)-2-propoxyiminoacetamido]-7-methoxy-3-(4-isopropyl-5-oxo-6-hydroxy-4,5-dihydro-1,2,4-triazin-3-ylthio)methyl-3-cephem-4-carboxylic acid, 7-[2-(2-aminothiazol-4-yl)-2-isobutoxyiminoacetamido]-7-methoxy-3-(4-methyl-5-oxo-6-hydroxy-3,4-dihydro-1,2,4-triazin-3-ylthio)methyl-3-cephem-4-carboxylic acid, and the corresponding lithium, potassium and sodium salts of each of the foregoing 7-methoxy cephalosporin compounds.

Exemplary of the biologically active compounds of the present invention wherein $R_2$ (in the above formula) is hydrogen are the following:

7-[2-(2-aminothiazol-4-yl)-2-methoxyiminoacetamido]-3-(4-ethyl-5-oxo-6-hydroxy-4,5-dihydro-1,2,4-triazin-3-ylthio)methyl-3-cephem-4-carboxylic acid, 7-[2-(2-aminothiazol-4-yl)-2-hydroxyiminoacetamido]-3-(4-methyl-5-oxo-6-hydroxy-4,5-dihydro-1,2,4-triazin-3-ylthio)methyl-3-cephem-4-carboxylic acid, 7-[2-(2-aminothiazol-4-yl)-2-ethoxyiminoacetamido]-3-(4-methyl-5-oxo-6-hydroxy-4,5-dihydro-1,2,4-triazin-3-ylthio)methyl-3-cephem-4-carboxylic acid, 7-[2-(2-aminothiazol-4-yl)-2-hydroxyiminoacetamido]-3-(4-ethyl-5-oxo-6-hydroxy-4,5-dihydro-1,2,4-triazin-3-ylthio)methyl-3-cephem-4-carboxylic acid, 7-[2-(2-aminothiazol-4-yl)-2-methoxyiminoacetamido]-3-(4-isopropyl-5-oxo-6-hydroxy-4,5-dihydro-1,2,4-triazin-3-ylthio)methyl-3-cephem-4-carboxylic acid, 7-[2-(2-aminothiazol-4-yl)-2-propoxyiminoacetamido]-3-(4-n-butyl-5-oxo-6-hydroxy-4,5-dihydro-1,2,4-triazin-3-ylthio)methyl-3-cephem-4-carboxylic acid, 7-[2-(2-aminothiazol-4-yl)-2-methoxyiminoacetamido]-3-(4-methyl-5-oxo-6-hydroxy-4,5-dihydro-1,2,4-triazin-3-ylthio)methyl-3-cephem-4-carboxylic acid, 7-[2-(2-aminothiazol-4-yl)-2-isobutoxyiminoacetamido]-3-(4-methyl-5-oxo-6-hydroxy-4,5-dihydro-1,2,4-triazin-3-ylthio)methyl-3-cephem-4-carboxylic acid, 7-[2-(2-aminothiazol-4-yl)-2-hydroxyiminoacetamido]-3-(4-n-butyl-5-oxo-6-hydroxy-4,5-dihydro-1,2,4-triazin-3-ylthio)methyl-3-cephem-4-carboxylic acid and the corresponding lithium, potassium and sodium salts of each of the foregoing cephalosporin acids.

A preferred group of the present cephalosporin compounds are those represented by the foregoing formula wherein $R_4$ is methyl or ethyl; most preferred of that group are those compounds represented when $R_4$ is methyl.

Also preferred compounds of the present invention are those represented when $R_1$ is hydrogen.

A further preferred group of the present compounds are those represented when $R_3$ is a $C_1$-$C_4$ alkyl group; the more preferred compounds within this group are those compounds represented when $R_3$ is methyl.

Another preferred group of the present cephalosporin compounds are those wherein R is hydrogen or an alkali metal cation; most preferred compounds within this group of the present cephalosporins are those compounds wherein, additionally, $R_2$ is hydrogen. These most preferred aminoacid cephalosporins of the present invention are those which particularly exhibit antibiotic activity. Compounds wherein R and $R_2$ are other than hydrogen are primarily useful as intermediates to the most active of the present compounds.

The novel cephalosporin carboxylic acids and their alkali metal salts are useful in combating infections in warm-blooded mammals when administered parenterally in nontoxic doses between about 10 and 500 mg./kg. of body weight. The actual dose employed will be varied in accordance with techniques well known by the medical community in the administration of cephalosporin antibiotics and will be determined by such factors as the nature and severity of the infection being treated, the frequency and duration of administration, the general condition of the patient and like factors.

The following examples are provided to further describe the invention and are not to be construed as limiting thereof.

PREPARATION 1

To 20 ml. of water were added 3.46 g. of 7-formamido-3-acetoxymethyl-3-cephem-4-carboxylic acid (12.0 mmole) and 2.0 g. of 3-mercapto-4-methyl-5-oxo-6-hydroxy-4,5-dihydro-1,2,4-triazine (12.55 mmole). The resulting mixture was stirred, and 1 N sodium hydroxide was added gradually until the pH remained at a constant 7.0. The resulting mixture was then stirred to about 55° C. for 26 hours. The resulting solution was concentrated to 20 ml. and acidified to pH 1.2 by addition with cooling of 3 N hydrochloric acid. The resulting precipitate was filtered and immediately placed into a bell jar to dry under vacuum. The dried material was ground in a mortar and pestle (2.75 g.), and was triturated three times, each with 150 ml. of boiling isopropyl alcohol. The isopropyl alcohol solution was evaporated to dryness and the residue was triturated twice with 30 ml. of ethyl acetate. The insoluble material was filtered, washed with ethyl acetate, and dried to give 1.56 g. of 7-formamido-3-(4-methyl-5-oxo-6-hydroxy-4,5-dihydro-1,2,4-triazin-3-ylthio)methyl-3-cephem-4-carboxylic acid.

Preparation 2

The product from Preparation 1 (0.74 g.) was stirred in 12 ml. of dry methanol, and 1.5 ml. of concentrated hydrochloric acid were added during which time complete solution occurred. After a short period of time, a white solid began to precipitate. Stirring was continued 1.7 hours, and the mixture became thick with a white precipitate. The precipitate was filtered and dried. The product (0.346 g.) was shown by TLC to be a highly pure sample of the hydrochloride of 7-amino-3-(4-methyl-5-oxo-6-hydroxy-4,5-dihydro-1,2,4-triazin-3-ylthio)-methyl-3-cephem-4-carboxylic acid.

Preparation 3

To a suspension of 3.71 g. (10 mmole) of 7-amino-3-(4-methyl-5-oxo-6-hydroxy-4,5-dihydro-1,2,4-triazin-3-ylthio)methyl-3-cephem 4-carboxylic acid in 50 ml. of methylene chloride and 50 ml. of methanol was added 1.94 g. (10 mmole) of diphenyldiazamethane. The reaction mixture was allowed to stir overnight at room temperature. An additional 500 mg. of diphenyldiazomethane was then added. After two hours the reaction mixture was filtered and the filtrate was concentrated in vacuo to an oil. This product was dissolved in about 25 ml. of methylene chloride, and the resulting solution was added dropwise to stirring hexane. A light yellow-brown amorphous solid formed. Filtration provided after drying 2.8 g. (52%) of benzhydryl 7-amino-3-(4-methyl-5-oxo-6-hydroxy-4,5-dihydro-1,2,4-triazin-3-ylthio)methyl-3-cephem-4-carboxylate: nmr(CDCl$_3$) δ 3.33 (s, 3, N-CH$_3$), 3.5 (m, 4, C$_2$-H, C$_3$-H), 4.86 (q, 2, CH$_6$-H, C$_7$-H), 7.0 (s, 1, benzhydryl C$\underline{H}$), 7.36 (s, 10, ArH).

EXAMPLE 1

To a solution of 0.55 g. (1 mmole) of benzhydryl 7-amino-3-(4-methyl-5-oxo-6-hydroxy-4,5-dihydro-1,2,4-triazin-3-ylthio)methyl-3-cephem-4-carboxylate and 886 mg. (2 mmole) of 2-(2-tritylamino-4-thiazolyl)-2-methoxyiminoacetic acid in 15 ml. of methylene chloride were added 208 mg. (1 mmole) of dicyclohexylcarbodiimide. After stirring the mixture six hours at room temperature, the reaction mixture was filtered. The filtrate was concentrated in vacuo to an oil which was then dissolved in ethyl acetate and washed successively with dilute sodium bicarbonate solution, water and brine. The ethyl acetate solution was then dried over anhydrous sodium sulfate and evaporated in vacuo to dryness to provide 800 mg. (83%) of benzhydryl 7-[2-(2-tritylamino-4-thiazolyl)-2-methoxyiminoacetamido]-3-(4-methyl-5-oxo-6-hydroxy-4,5-dihydro-1,2,4-triazin-3-ylthio)methyl-3-cephem-4-carboxylate as a red amorphous solid: nmr(CDCl$_3$, DMSO d-6) δ 3.3 (s, 3, N-CH$_3$), 3.7 (s, 2, C$_2$-H), 4.1 (s, 3, -OCH$_3$), 5.2 (d, 1, J=5.0 Hz, C$_6$-H), 5.8 (q, 1, J=5.0 and 8.0 Hz, C$_7$-H), 6.8 (s, 1, thiazolyl C$_5$-H), 7.0 (s, 1, benzhydryl CH) and 7.4 (s, 25, trityl and benzhydryl ArH).

EXAMPLE 2

About 500 mg. of the product benzhydryl ester from Example 1 above was suspended in 10 ml. of 50% aqueous formic acid and heated on a steam bath for five minutes. The mixture was then stirred at 50° to 60° C. on a hot plate for 45 minutes. After allowing the mixture to cool to about 30°, it was filtered and the filtrate was concentrated in vacuo to an oily residue. Trituration of the residue with ethyl alcohol provided upon filtration a light brown amorphous solid which was then washed with methylene chloride. Yield 161 mg. (56%). High pressure liquid chromatography shows the product to be very pure: nmr(DMSO d-6) δ 3.29 (s, 3, N-CH$_3$), 3.65 (s, 2, CH$_2$-H), 3.03 (s, 3, OCH$_3$), 4.10 (q, 2, C$_3$,-H), 5.15 (d 1, J=5.0 Hz, C$_6$-H), 5.77 (q, 1, J=5.0 and 8.0 Hz, C$_7$-H), 6.73 (s, 1, thiazolyl C$_5$-H), 7.20 (s, 2, NH$_2$), 9.58 (d, 1, J=8.0 Hz, side chain NH).

I claim:

1. A compound of the formula

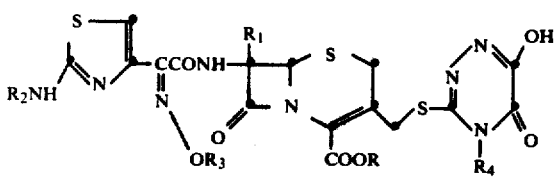

wherein in the above formula
R is hydrogen, an alkali metal cation, or a carboxylic acid protecting group;
$R_1$ is hydrogen or methoxy;
$R_2$ is hydrogen or an amino protecting group;
$R_3$ is hydrogen or $C_1$–$C_4$ alkyl; and
$R_4$ is $C_1$–$C_4$-alkyl.

2. The compound of claim 1 wherein R is a carboxylic acid protecting group.

3. The compound of claim 2 wherein R is benzhydryl.

4. The compound of claim 2 wherein R is acetoxymethyl, 1-acetoxyethyl, pivaloyloxymethyl, 1-pivaloyloxyethyl, carboethoxyoxymethyl, 1-carboethoxyoxyethyl or phthalidyl.

5. The compound of claim 1 wherein R is hydrogen or an alkali metal cation.

6. The compound of claim 5 wherein $R_1$ is methoxy.

7. The compound of claim 5 wherein $R_1$ is hydrogen.

8. The compound of claim 7 wherein $R_3$ is $C_1$–$C_4$ alkyl.

9. The compound of claim 8 wherein $R_3$ is methyl.

10. The compound of claim 9 wherein $R_2$ is hydrogen.

11. The compound of claim 10 wherein $R_4$ is methyl.

12. The compound of claim 11 said compound being 7-[2-(2-aminothiazol-4-yl)-2-methoxyiminoacetamido]-3-(4-methyl-5-oxo-6-hydroxy-4,5-dihydro-1,2,4-triazin-3-ylthio)-methyl-3-cephem-4-carboxylic acid (syn isomer).

* * * * *